United States Patent [19]
Miller

[11] Patent Number: 4,957,734
[45] Date of Patent: Sep. 18, 1990

[54] TREATMENT OF CERTAIN SKIN MALIGNANCIES AND PRE-MALIGNANT SKIN LESIONS, HERPES ZOSTER AND PSORIASIS

[75] Inventor: Daniel G. Miller, Scarsdale, N.Y.

[73] Assignee: Exovir, Inc., Great Neck, N.Y.

[21] Appl. No.: 70,592

[22] Filed: Jul. 6, 1987

Related U.S. Application Data

[63] Continuation of Ser. No. 851,885, Apr. 11, 1986, abandoned, which is a continuation of Ser. No. 651,277, Sep. 14, 1984, abandoned, which is a continuation of Ser. No. 388,260, Jun. 14, 1982, abandoned.

[51] Int. Cl.$^5$ .............................................. A61K 37/66
[52] U.S. Cl. .................................... 424/85.7; 424/85.4
[58] Field of Search .................... 424/85.2, 85.4, 85.5, 424/85.6, 85.7

[56] References Cited

U.S. PATENT DOCUMENTS

| 4,020,183 | 4/1977 | Asculai et al. | 424/341 |
| 4,139,630 | 2/1979 | Asculai et al. | 424/285 |
| 4,507,281 | 3/1985 | Asculai et al. | 424/85.7 |

FOREIGN PATENT DOCUMENTS 102519  8/1980  Japan .

OTHER PUBLICATIONS

Borzov, M., et al., Vestnik Dermatologii i Venerologii, vol. 45, No. 9, pp. 14–17, 1971.
Yancey, K., et al., J. American Academy of Dermatology, vol. 46, No. 4, pp. 10–13, 1972.
Ikic, D., et al., the Lancet, pp. 1025–1027, May 9, 1981.
Igoshin, Y., et al., Vestnik Dermatologii i Vernerologii, vol. 46, No. 4, pp. 10–13, 1972.
Pazin, G., et al., J. Interferon Research, vol. 2, pp. 235–243, 1982.
Ikic, D., et al., Proc. Symposium on Clinical Use of Interferon, Oct. 1975, Ikibic, Drago, et al., pp. 235–238.

*Primary Examiner*—Blondel Hazel
*Attorney, Agent, or Firm*—Cooper & Dunham

[57] ABSTRACT

A composition consisting essentially of human leukocyte interferon and an antiviral surfactant, such as the non-ionic surfactant, nonylphenoxypolyethoxy ethanol, and a physiologically acceptable carrier therefor, has been found to be useful for the treatment of malignant and pre-malignant skin lesions and skin lesions associated with herpes zoster and psoriasis by topically administering or applying the composition to the affected skin area.

2 Claims, No Drawings

TREATMENT OF CERTAIN SKIN MALIGNANCIES AND PRE-MALIGNANT SKIN LESIONS, HERPES ZOSTER AND PSORIASIS

This is a continuation of application Ser. No. 851,885 filed Apr. 11, 1986, now abandoned which, in turn, is a continuation of application Ser. No. 651,277 filed Sept. 14, 1984 now abandoned which, in turn, is a continuation of application Ser. No. 388,260 filed June 14, 1982 now abandoned.

BACKGROUND OF THE INVENTION

This invention relates to a method for treatment of skin malignancies and pre-malignant skin lesions, including squamous cell carcinoma, basal cell carcinoma, actinic keratosis, and leukoplakia. This invention also relates to a method for treatment of psoriasis and herpes zoster.

Basal cell carcinomas, which may appear as small, shiny, firm nodules or ulcerated crusted lesions on the skin, are generally treated by electrodesiccation and curettage, surgical excision or X-ray therapy. In about 5% of cases, recurrences occur. Such recurrences are treated typically with further excision or Moh's chemosurgery, i.e., microscopically controlled excision after chemical fixation of the tissue.

Squamous cell carcinoma arises from the malpighian cells of the epithelium. The tumor generally begins as a small red papule or plaque with a scaly or crusted surface. Subsequently, it becomes nodular. Eventually, the lesion ulcerates and invades the underlying tissue. As with basal cell carcinoma, squamous cell carcinoma is heated with electrodesiccation and curettage, surgical excision or X-ray therapy.

Pecancerous keratotic lesions, actinic keratoses, are the frequent consequence of many years of overexposure exposure to sunlight. The keratoses are usually hard, and gray to dark in color. Such lesions are generally treated by topical application of fluorouracil (5-fluorouracil). However, if the lesions become malignant, topical application of fluorouracil is not recommended as the rate of recurrence is unacceptably high with such therapy.

Leukoplakia, hyperkeratinization of the oral mucosa, is generally believed to result from several factors, local or systemic, acting independently or in combination, such as: tobacco, alcohol, chronic irritation from such causes as cheek biting, ill-fitting dentures, sharp, broken or worn-down teeth or spicy foods, syphilis, vitamin deficiency, hormonal changes and *Candida albicans*. Leukoplakia lesions vary from a small, well-localized white patch to a diffuse area involving much of the oral mucosa, and from a smooth, flat, or slightly elevated, translucent white plaque to a thick, fissured papillomatous lesion that is firm to palpation. Treatment of leukoplakia generally comprises initial removal or elimination of any recognizable irritating factors, such as tobacco or faulty restoration or prosthetic devices, to chemical irritants, and total excision or cauterization of the localized lesions. Large lesions may be removed by a series of "stripping" operations. The patient should additionally be re examined periodically and any legions subsequently located biopsied because of the precancerous nature of the disease. Additionally, leukoplakia may be involved in lesions of the vulva and anus. When involved with the vulva, leukoplakia is treated by total vulvectomy.

Psoriasis is characterized by skin lesions which are sharply demarcated, usually non-pruritic, erythematous papules or plaques covered with overlappinq, silvery or lightly opalescent, shiny scales. The typical course of psoriasis is chronic remission and recurrence, which vary in frequency and duration. Psoriasis varies in severity from one or two lesions to a widespread dermatosis, to psoriatic arthritis or exfoliation. Treatment depends upon the extent and severity of the involvement. The simplest form of treatment, topical application of lubricants, keratolytics and corticosteroids, is initially employed. Systemic antimetabolites should be used only in severe skin or joint involvement because of their potential adverse effects. Exposure to ultraviolet light has been found helpful in the treatment of psoriasis. Methotrexate taken orally is generally an effective treatment in severe disabling psoriasis which has not responded to topical therapy. However, because of the toxicity of methotrexate, hematological, renal and hepatic functions of the patient must be carefully monitored.

Herpes zoster is a virus-related, acute CNS infection involving primarily the dorsal root ganglia, and characterized by vesicular eruption and neuralgic pain in the cutaneous area supplied by peripheral sensory nerves arising in the affected root qanqlia. Herpes zoster may be activated by local lesions or by systemic disease, among other reasons. Prodromal symptoms of chills and fever, malaise and GI disturbances may be present for three or four days before the distinctive features of the disease develop. On about the fourth or fifth day, characteristic crops of vesicles on an erythematous base appear, following the cutaneous distribution of one or more posterior root ganglia. There is no specific treatment for herpes zoster. Early systemic application of a corticosteroid, however, generally relieves pain.

It would thus be desirable to provide a method for treatment of malignant and pre-malignant skin lesions, which comprises topical administration of an effective agent.

It would also be desirable to provide an effective method for treatment of malignant and pre-malignant skin lesions which employs topical application of a non-toxic agent.

It would also be desirable to provide an effective method for treatment of psoriasis comprising topical administration of a non-toxic and relatively non-antigenic agent.

It would further be desirable to provide a method for treatment of herpes zoster comprising topical administration of an effective, therapeutic agent.

Human interferon is known to protect cells against viral infection. Human interferon is produced by cells in reaction to the presence of specific inducers, such as viruses. It may be produced in vivo by the cells of living organisms, or it may be produced in vitro by cell cultures in response to the presence of the inducer. There are now known to be three main varieties of human interferon: leukocyte ($\alpha$), fibroblast ($\beta$) and inunune ($\gamma$). Additionally, there are also known to be several subvarieties of human leukocyte ($\alpha$) and fibroblast ($\beta$) interferon.

Human interferon is nontoxic and relatively nonantigenic in humans. It is an effective agent against a broad spectrum of viruses, including herpes simplex virus. For example, U.S. Pat. No. 4,061,538 (Dorner et al.) and U.S. Pat. No. 4,184,917 (Dorner et al.) disclose a method of treating herpes simplex viral infections by administering structurally modified interferons to the patient. The method of administration disclosed in the Dorner patents is systemic. Several published reports also disclose treatment of herpetic eye infections by topical administration of human interferon. For example, see D. Naumann-Haefelin et al. in *Infection and Immunicyt*, 17:458 (1977) and B. R. Jones et al. in *Lancet* ii:128 (976).

It has also been recently discovered that nonionic surface active agents (such as are employed as spermicides in vaginal contraceptives) are effective in treatment of viral skin diseases. For example, in Asculai, S. S. et al; *Antimicrobial Agents and Chemotherapy*, 13:686 (1978), it is reported that certain nonionic surface active agents rapidly reduce the infectivity of herpes simplex viruses (HSV-1) and HSV-2) in vitro. The nonionic surface active agents which inactivated the infectivity of the viruses were those possessing ether or amide linkages between the hydrophilic and the hydrophobic portions of the molecule. See also U.S. Pat. No. 4,020,183 (Asculai et al.) and U.S. Pat. No. 4,139,630 (Asculai et al.) The therapeutic effect of such nonionic surfactants was attributed in part to their potential to dissolve the lipid-containing envelope of the virus. The non-ionic surfactants were also reported to partially destroy the nucleocapsid of the virus.

Topical administration of human interferon and activiral surfactants, preferably a nonionic surfactant, in the treatment of herpes simplex legions (both HSV-1 and HSV-2) has been disclosed in co-pending and co-assigned U.S. patent application Ser. No. 311,035 (Asculai et al.), filed Oct. 3, 1981.

Accordingly, it is an object of the present invention to provide a method for treatment of malignant and pre-malignant skin lesions, herpes zoster and psoriasis.

It is also an object of the present invention to provide a method of treatment of skin malignancies and pre-malignant lesions, herpes zoster and psoriasis which comprises topical treatment of the affected skin area with a pharmaceutical composition.

It is another object of this invention to provide a method for treatment of malignant and pre-malignant skin lesions by topical administration of a nontoxic pharmaceutical composition.

It is a further object of this invention to provide a method for treatment of skin lesions produced by squamous cell carcinoma, basal cell carcinoma, actinic keratosis, leukoplakia, psoriasis and herpes zoster which comprises administration of a relatively nonantigenic pharmaceutical preparation.

SUMMARY OF THE INVENTION

A method for treating skin malignancies, pre-malignant skin lesions, and lesions associated with psoriasis and herpes zoster comprises topically administering to the affected skin area an effective amount of a composition comprising about $10^2$–$10^8$ IU of human interferon, about 0.1% to 20% by weight of an antiviral surface active agent, and a physiologically acceptable carrier The topical administration could be achieved by direct application of the pharmaceutical product with or without an occlusive dressing. The method of treatment for malignant and pre-malignant skin lesions would preferably involve daily application of a composition containing human interferon and an antiviral surface active agent with an occlusive dressing. Such treatment of the lesions would preferably continue for ten days, at which point evaluation of the treatment would be made.

DETAILED DESCRIPTION OF THE INVENTION

The novel method of treatment of malignant skin lesions, pre-malignant skin lesions, and skin lesions associated with psoriasis and herpes zoster comprises topical administration of an effective amount of a pharmaceutical composition containing human interferon and an antiviral surface active agent, contained in a physiologically acceptable carrier. The interferon used in the pharmaceutical composition may be any of the known varieties or subvarieties of human interferon. Thus, the pharmaceutical composition may contain human leukocyte ($\alpha$), fibroblast ($\beta$), or one ($\gamma$) interferon. Furthermore, the interferon may be prepared by classical culture methods or by recombinant DNA methods. An effective dosage of human interferon for treating the skin lesions in accordance with the practices of the present invention is about $10^2$–$10^8$ IU and preferably $10^4$–$10^6$ IU.

The antiviral surface active agent of the pharmaceutical composition may be anionic, cationic, or, preferably, nonionic. Antiviral surface active agents are known in the art. Suitable anionic surfactants include sodium alkylsulfonates, and sodium alkylbenzenesulfonates. Suitable cationic surfactants include quaternary ammonium detergents, such as cetyl pyridinium chloride and benzalkonium chlorides.

Nonionic surface active agents are preferred in the pharmaceutical preparations employed with the method of the present invention. In contrast to cationic and anionic (and also ampholytic) surface active agents the nonionics contain no ionizable groups and have no surface charge. They depend upon their entire molecule for surface activity. Almost any hydrophobic compound which has in its structure a carboxy, hydroxy, amido or amino group with a free hydrogen attached to the nitrogen, can be reacted with ethylene oxide to form a nonionic surfactant. At least three groups of nonionic surfactants are recognized: (a) those having an ether linkage between the hydrophilic and hydrophobic portions of the molecule; (b) those having an ester or ether-ester linkage; and (c) those having an amide linkage. Non-ionic surfactants having at least one ether or amide linkage are preferred for purposes of the present invention. Examples of such preferred nonionic surfactants include the following: nonylphenoxy-polyethoxy ethanol available under the trade name Nonoxynol-9); p-diisobutylphenoxy-polyethoxy ethanol. (available under the trade name Triton X-100); polyoxyethylene (10) oleyl ether (available under the trade name Brij-97 ; and onyx-ol (available under the . trade name Onyx-ol 345).

An effective amount of an antiviral surface active agent in a pharmaceutical composition employed in the method of the present invention comprises about 0.1% to 20% by weight of the pharmaceutical composition. The preferred range is about 1% to about 5% by weight.

The balance of the pharmaceutical composition employed in the method of the present invention comprises an inert, physiologically acceptable carrier. The carrier should not react with or otherwise reduce the effectiveness of the active ingredients. Suitable physiologically acceptable carriers include: water; ethanol; polyethylene glycol; mineral oil; petrolatum; propylene glycol; and the like. The pharmaceutical composition are preferably prepared in lotion, cream, oil or emulsion formulations for administration in accordance with the present invention.

The following are examples of suitable formulations to be used in the method of the present invention containing a nonionic surfactant and human interferon.

| LOTION | |
|---|---|
| Propylene glycol | 24.75 ml |
| Triethanolamine | 1.00 ml |
| Water | 7.00 ml |
| Oleic acid | 1.50 gm |
| Polyethylene glycol monostearate | 10.50 gm |
| Silicon fluids | 10.00 ml |
| Carbopol-934 (2% mucilage) | 50.00 ml |
| Human leukocyte ($\alpha$) interferon | $10^6$–$10^8$ IU |
| CREAM A | |
| White petrolatum | 41.00 gm |
| Microcrystalline wax | 3.00 gm |
| Fluid lanolin | 10.00 gm |
| Sorbitan monooleate | 4.75 gm |
| Polysorbate-80 | 0.25 gm |
| Purified water | 41.00 gm |
| Human leukocyte ($\alpha$) interferon | $10^6$–$10^8$ IU |
| CREAM B | |
| Spermaceti | 7.5% |
| White was | 12.0% |
| Mineral oil | 56.0% |
| Sodium borate | 0.5% |
| Sorbitan monooleate | 5.0% |
| Water | 19.0% |
| Human leukocyte ($\alpha$) interferon | $10^5$–$10^7$ IU |

The treatment of skin malignancies such as squamous cell carcinoma and basal cell carcinoma and premalignant lesions such as actinic keratosis and leukoplakia according to the present invention involves topical application of a pharmaceutical composition containing an effective amount of human interferon and antiviral surface active agent, such as described above. The topical administration could be accomplished with or without an occlusive dressing, but preferably with an occlusive dressing. The lesions are preferably treated daily for a period of about ten (10) days by topical administration of a pharmaceutical composition containing interferon and an antiviral surfactant. After such time, the lesions would be evaluated and a determination made whether further or continued treatment should be undertaken. For example, observation should be made for improvement in lesions or for possible new lesions.

The present method of treatment is also useful in cases where squamous or basal cell carcinomas have been surgically removed, but the tumor margins of the specimen showed tumor cells. The present method would be employed as a form of prophylactic therapy, with monitoring for recurrences.

Although ten (10) day courses of daily application with an occlusive dressing are preferable in the treatment of malignant and pre-malignant skin lesions, modifications can be readily made as necessary in treatment of specific cases.

In treatment of herpes zoster according to the present invention, topical application, preferably with an occlusive dressing, would be made of a pharmaceutical composition containing interferon and an antiviral surfactant, as described above. Application would be made two to three times daily until there was evidence of healing. By using the method of the present invention, pain associated with herpes zoster is alleviated because of local healing. Additionally, use of the method of the present invention in treatment of herpes zoster has been found to prevent postherpetic neuralgia. The lesions associated with herpes zoster have been determined to heal faster than if left untreated using the method of the present invention.

In the treatment of psoriasis according to the present invention, repeated courses of topical application of interferon and an antiviral surfactant in a physiologically acceptable carrier according to the present invention would be required. Psoriasis is a chronic, recurring condition, for which there is no known cure. Since large areas of the skin are often involved, a plastic occlusive dressing would preferably be used to insure absorption into the skin of the pharmaceutical composition containing human interferon and an antiviral surfactant. Additionally, since large areas may be involved and hence require treatment, a significant amount of the human interferon would be absorbed into the bloodstream. Such may have a favorable effect on the systemic aspects of psoriasis, i.e., psoriatic arthritis.

Topical administration according to the present invention may be effected by applying a small amount (e.g., about 1 ml) of the compositions containing human interferon and an antiviral surfactant directly to and in areas adjacent to the site of lesions with a cotton swab, soft brush, sponge, or the like. The quantity applied would be dependent on the size of the lesions being treated. Any quantity sufficient to cover the area of the lesions is effective.

In addition to direct application, the pharmaceutical compositions containing human interferon and an antiviral surfactant may be administered topically by various other methods. For example, the compositions may be delivered to the affected skin region in microencapsulated form. The pharmaceutical compositions may also be delivered in a foam, by spray, suppository, etc.

In another embodiment, this invention comprises treatment of the malignant or pre-malignant skin lesions, psoriasis and herpes zoster with a cosmetic composition an containing effective amounts of human interferon, an antiviral surface active agent, and a physiologically acceptable cosmetic carrier. Additional components, for example, skin softeners, may be included in the cosmetic formulation. Cosmetic formulations are known in the art and are usually hypoallergenic and pH controlled. Cosmetic formulations according to the present invention contain less human interferon and antiviral surface active agent than pharmaceutical preparations. The preferred range of dosage of human interferon is $10^3$–$10^5$ IU and the preferred range of amount of antiviral surface active agent is 0.1% to 1% by weight in the composition. A nonionic antiviral surface active agent again is preferred. A typical cosmetic formulation according to the present invention is recited below.

| COSMETIC CREAM | |
|---|---|
| Beeswax | 12.1% |
| Spermaceti | 12.6% |
| Sweet almond oil | 54.4% |
| Borax | 0.5% |
| Rosewater | 19.4% |
| Onyxol | 1.0% |
| Human leukocyte ($\alpha$) interferon | $10^3$–$10^5$ IU |

While the invention has been described by reference to specific embodiments, this was for purposes of illustrations only and should not be construed to limit the spirit or the scope of the invention.

What is claimed is:

1. A method for the treatment of malignant and premalignant skin lesions and skin lesions associated with herpes zoster and psoriasis which comprises topically administering to the affected skin area an amount of a composition consisting essentially of affective amount of human leukocyte interferon and an effective antiviral amount of the non-ionic surfactant nonylphenoxypolyethoxyethanol and a physiologically acceptable carrier.

2. A method in accordance with claim 1 herein said composition contains from about 1% to about 5% by weight of said surfactant.

* * * * *